US010357202B2

(12) United States Patent
Cheung Hyen et al.

(10) Patent No.: US 10,357,202 B2
(45) Date of Patent: *Jul. 23, 2019

(54) SYSTEM AND METHOD FOR NON-INTRUSIVE HEALTH MONITORING IN THE HOME

(71) Applicant: Universal Electronics Inc., Santa Ana, CA (US)

(72) Inventors: David Chong Cheung Hyen, Singapore (SG); Patrick H. Hayes, Mission Viejo, CA (US)

(73) Assignee: Universal Electronics Inc., Santa Ana, CA (US)

(*) Notice: Subject to any disclaimer, the term of this patent is extended or adjusted under 35 U.S.C. 154(b) by 723 days.

This patent is subject to a terminal disclaimer.

(21) Appl. No.: 14/531,366

(22) Filed: Nov. 3, 2014

(65) Prior Publication Data
US 2015/0051456 A1  Feb. 19, 2015

Related U.S. Application Data

(63) Continuation of application No. 12/956,444, filed on Nov. 30, 2010, now Pat. No. 8,905,927.

(51) Int. Cl.
A61B 5/00 (2006.01)
H04N 21/422 (2011.01)
(Continued)

(52) U.S. Cl.
CPC .......... A61B 5/6898 (2013.01); A61B 5/0002 (2013.01); A61B 5/02055 (2013.01);
(Continued)

(58) Field of Classification Search
USPC ................................. 600/300–301
See application file for complete search history.

(56) References Cited

U.S. PATENT DOCUMENTS 4,959,810 A   9/1990  Darbee et al.
5,455,570 A   10/1995 Cook et al.
(Continued)

FOREIGN PATENT DOCUMENTS

EP   1304071      4/2003
JP   2005/241181   9/2005
(Continued)

OTHER PUBLICATIONS

European Patent Office, Extended European Search Report issued on EP patent application No. 11844942.0, 10 pages.
(Continued)

Primary Examiner — Niketa I Patel
Assistant Examiner — Shirley X Jian
(74) Attorney, Agent, or Firm — Greenberg Traurig, LLP

(57) ABSTRACT

A hand-held device, such as a remote control, is provided for operation of a consumer appliance and is equipped with one or more biometric sensors to capture and report on the health condition of a user of the hand-held device. The data captured by such a hand-held device may be evaluated locally in the hand-held device itself or may be conveyed to a target consumer appliance either for local evaluation by that consumer appliance or for onward transmission to a central off-site monitoring service.

19 Claims, 7 Drawing Sheets

(51) Int. Cl.
*H04N 21/442* (2011.01)
*H04N 21/61* (2011.01)
*H04N 21/81* (2011.01)
*A61B 5/0205* (2006.01)
*A61B 5/11* (2006.01)

(52) U.S. Cl.
CPC .............. *A61B 5/11* (2013.01); *A61B 5/6826* (2013.01); *A61B 5/72* (2013.01); *A61B 5/746* (2013.01); *A61B 5/747* (2013.01); *A61B 5/7475* (2013.01); *H04N 21/42201* (2013.01); *H04N 21/42204* (2013.01); *H04N 21/44218* (2013.01); *H04N 21/6168* (2013.01); *H04N 21/814* (2013.01); *A61B 5/0004* (2013.01); *A61B 2505/07* (2013.01)

(56) References Cited

U.S. PATENT DOCUMENTS

| | | | | |
|---|---|---|---|---|
| 5,601,435 | A * | 2/1997 | Quy | A61B 5/044 345/501 |
| 5,776,056 | A * | 7/1998 | Bu | A61B 5/0017 600/301 |
| 5,933,136 | A * | 8/1999 | Brown | G06F 19/3418 348/61 |
| 6,144,837 | A * | 11/2000 | Quy | A61B 5/044 345/501 |
| 6,238,337 | B1 * | 5/2001 | Kambhatla | A61B 5/0002 600/300 |
| 6,419,630 | B1 * | 7/2002 | Taylor, Jr. | A61B 5/02055 128/903 |
| 6,731,962 | B1 | 5/2004 | Katarow et al. | |
| 6,830,549 | B2 * | 12/2004 | Bui | A61B 5/0002 600/549 |
| 6,893,396 | B2 * | 5/2005 | Schulze | A61B 5/0022 128/903 |
| 6,906,533 | B1 * | 6/2005 | Yoshida | A61B 5/0537 324/611 |
| 6,968,375 | B1 * | 11/2005 | Brown | A61B 5/0002 600/301 |
| 7,046,185 | B2 | 5/2006 | Griesau et al. | |
| 7,102,531 | B2 * | 9/2006 | Maeda | A61B 5/0537 324/611 |
| 7,154,428 | B2 | 12/2006 | de Clercq et al. | |
| 7,261,691 | B1 | 8/2007 | Asomani | |
| 7,315,736 | B2 | 1/2008 | Jenkins | |
| 7,382,247 | B2 | 6/2008 | Welsh et al. | |
| 7,423,526 | B2 | 9/2008 | Despotis | |
| 7,564,369 | B1 * | 7/2009 | Adams | G08C 23/04 340/12.53 |
| 7,584,108 | B2 * | 9/2009 | Brown | G06F 19/3418 705/2 |
| 7,590,549 | B2 * | 9/2009 | Brown | G06F 19/3418 705/2 |
| 7,620,212 | B1 * | 11/2009 | Allen | G06K 9/0004 340/5.53 |
| 8,161,290 | B2 * | 4/2012 | McQuaide, Jr. | H04B 1/202 713/150 |
| 8,334,789 | B2 * | 12/2012 | Nakada | A61B 5/0002 340/573.1 |
| 8,780,278 | B2 * | 7/2014 | Gulati | H04N 5/144 348/552 |
| 9,492,088 | B2 * | 11/2016 | Chapusot | A61B 5/0022 |
| 2002/0062069 | A1 * | 5/2002 | Mault | A61B 5/0002 600/300 |
| 2002/0107433 | A1 * | 8/2002 | Mault | A61B 5/044 600/300 |
| 2002/0174425 | A1 * | 11/2002 | Markel | H04N 7/165 725/13 |
| 2003/0126593 | A1 * | 7/2003 | Mault | A61B 5/0002 725/10 |
| 2003/0181817 | A1 * | 9/2003 | Mori | A61B 5/0002 600/500 |
| 2003/0208110 | A1 * | 11/2003 | Mault | A61B 5/0002 600/300 |
| 2003/0226695 | A1 * | 12/2003 | Mault | A61B 5/0002 177/25.16 |
| 2004/0222979 | A1 * | 11/2004 | Knighton | G06F 3/0221 345/184 |
| 2005/0066370 | A1 * | 3/2005 | Alvarado | G08C 17/00 725/80 |
| 2006/0004303 | A1 * | 1/2006 | Weidenhaupt | A61B 5/157 600/583 |
| 2006/0234202 | A1 * | 10/2006 | Brown | A61B 5/044 434/323 |
| 2007/0249916 | A1 | 10/2007 | Pesach et al. | |
| 2007/0299322 | A1 * | 12/2007 | Miyajima | A61B 5/0008 600/301 |
| 2008/0034217 | A1 * | 2/2008 | McQuaide | H04B 1/202 713/186 |
| 2008/0049980 | A1 * | 2/2008 | Castaneda | G06K 9/00013 382/115 |
| 2008/0268413 | A1 * | 10/2008 | Leichner | G06F 19/322 434/262 |
| 2008/0319797 | A1 * | 12/2008 | Egami | G06F 19/363 705/3 |
| 2009/0043180 | A1 | 2/2009 | Tschautscher et al. | |
| 2009/0137890 | A1 * | 5/2009 | Burnes | A61M 5/14244 600/365 |
| 2009/0251619 | A1 * | 10/2009 | Seidel | H04N 5/4403 348/734 |
| 2009/0322513 | A1 | 12/2009 | Hwang et al. | |
| 2010/0005117 | A1 * | 1/2010 | Stut | A61B 5/0002 707/E17.044 |
| 2010/0222645 | A1 | 9/2010 | Nadler et al. | |
| 2010/0235177 | A1 | 9/2010 | Wischmann et al. | |
| 2011/0014954 | A1 * | 1/2011 | Dossas | A61B 5/0002 455/566 |
| 2011/0221622 | A1 * | 9/2011 | West | G08C 17/02 341/176 |
| 2013/0031373 | A1 * | 1/2013 | Shang | G06F 21/10 713/189 |
| 2014/0316285 | A1 * | 10/2014 | Dossas | A61B 5/0002 600/483 |

FOREIGN PATENT DOCUMENTS

| | | |
|---|---|---|
| WO | 2005/117522 | 12/2005 |
| WO | 2007/028107 | 3/2007 |
| WO | 2008/014154 | 1/2008 |
| WO | 2010/020924 | 2/2010 |

OTHER PUBLICATIONS

Guillen S. et al., Multimedia Telehomecare Systems Using Standard TV Set, IEEE Transactions on Biomedical Engineering, Dec. 1, 2002, 7 pages.

The International Bureau of WIPO, International Preliminary Report on Patentability issued on PCT Appln. No. US2011/062191, dated Jun. 13, 2013, 6 pages.

* cited by examiner

SYSTEM AND METHOD FOR NON-INTRUSIVE HEALTH MONITORING IN THE HOME

RELATED APPLICATION INFORMATION

This application claims the benefit of and is a continuation of U.S. application Ser. No. 12/956,444, filed on Nov. 30, 2010, which application is incorporated herein by reference in its entirety.

BACKGROUND

Various methods have previously been proposed to provide non-invasive, preferably home-based, monitoring of health conditions such as blood pressure, temperature, pulse rate, blood sugar, etc. For example U.S. Published Patent Application No. 2007/0249916 describes a wearable apparatus for continuous non-invasive monitoring of a patient's blood glucose level. Japanese laid-open Patent Application No. JP 2005-241181 describes a remote control apparatus for an air conditioner which incorporates a skin moisture sensor. U.S. Pat. No. 7,423,526 and U.S. Published Patent Application No. 2009/0322513 both describe wearable bracelet-type devices incorporating various physiological monitoring technologies. Furthermore, wearable devices for use either in a hospital or in a home environment and capable of wirelessly reporting and/or alarming various physiological parameters to a central monitoring location have been previously described in the art, for example as may be found in U.S. Pat. No. 7,382,247, 7,315,736, 7,261,691, or 6,731,962. These health monitoring solutions typically require some type of specialized sensing apparatus in the form of a wearable bracelet, etc., together with a separate purpose-specific unit to receive and relay the wireless reporting signals.

Controlling devices, for example remote controls, for use in issuing commands to entertainment and other appliances, and the features and functionality provided by such controlling devices are well known in the art and have become a ubiquitous part of the modern home for use in conjunction with various appliances such as cable set top boxes, satellite receivers, etc. Such controlling devices may be universal, that is, capable of controlling multiple appliance types of different manufacture, unified, that is, capable of controlling multiple appliance types of the same manufacture, or dedicated, that is, capable only of controlling a single appliance of a specific manufacture. Descriptions of such controlling devices may be found, for example, in U.S. Pat. Nos. 4,959,810, 5,455,570, 7,046,185, or 7,154,428.

A synergistic combination of these two functionalities is proposed herein.

SUMMARY

In an order to facilitate a health monitoring service offered in conjunction with a consumer appliance, such as an interactive cable or satellite set top box ("STB"), an Internet connected TV, an add-on media consolidation device (for example as currently offered as the Logitech "Revue," D-Link "Boxee" Box, Western Digital "TV Live"), etc., an exemplary hand-held device such as a remote control provided for operation of the consumer appliance may be equipped with various biometric sensors to capture and report on the health condition of the user of the hand-held device. The data captured by such a hand-held device may be evaluated locally in the hand-held device itself or may be conveyed to a target consumer appliance either for local evaluation by that consumer appliance or for onward transmission to a central off-site monitoring service. Alternatively, where the hand-held device itself is capable of wide area communication (for example is WiFi equipped), the captured information may be directly conveyed to an off-site monitoring service. If one or more of the measured health parameters falls outside the normal range, various actions may be taken either by the local hand-held device/consumer appliance or by the off-site monitoring service. Such actions may range in scope from presenting a warning signal/message through raising a local alarm to automatic dispatch of emergency personnel.

A better understanding of the objects, advantages, features, properties and relationships of the subject system and method will be obtained from the following detailed description and accompanying drawings which set forth illustrative embodiments and which are indicative of the various ways in which the principles of the subject system and method may be employed.

BRIEF DESCRIPTION OF THE DRAWINGS

For a better understanding of the various aspects of the subject system and method, reference may be had to preferred embodiments shown in the attached drawings in which.

DETAILED DESCRIPTION

Figure 1:
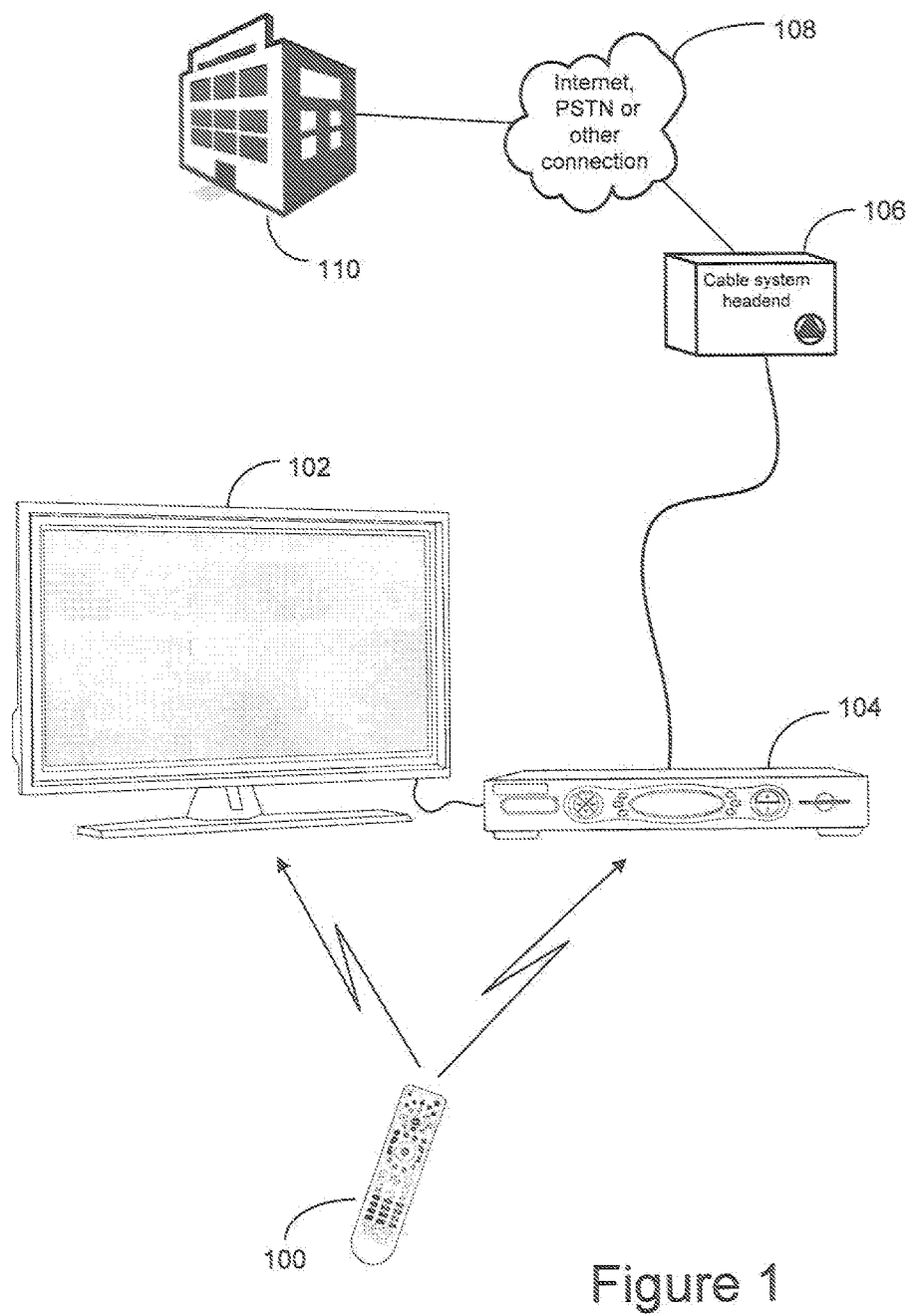
FIG. 1 illustrates an exemplary system in which an exemplary controlling device according to the instant invention may be used.

Turning now to FIG. 1, there is illustrated an exemplary system in which a controlling device 100 is configured to control various controllable appliances, such as, for example, a television 102 and a set top box ("STB") 104. As is known in the art, the controlling device 100 may be capable of transmitting commands to the appliances in response to user activation of various command function keys using any convenient IR, RF, Point-to-Point, or networked protocol, to cause the appliances to perform operational functions. While illustrated in the context of a television 102 and STB 104, it is to be understood that controllable appliances may include, but need not be limited to, televisions, VCRs, DVRs, DVD players, cable or satellite converter set-top boxes ("STBs"), amplifiers, CD players, game consoles, home lighting, drapery, fans, HVAC systems, thermostats, personal computers, etc. As is also known in the art, controlling device 100 may also include means for use in configuring the operation of controlling device 100, e.g., changing operational modes, selecting active key sets, etc. In a particular illustrative embodiment, in addition to this conventional functionality, controlling device 100 may further include means for monitoring certain biomedical parameters representative of the health status of a user of the controlling device 100, and in the embodiment illustrated, reporting such data to an exemplary STB 104 or like consumer appliance for onward transmission to a monitoring center service 110 (e.g., having a server, data repository, and appropriate programming/instructions) via a cable system headend 106 (e.g., having a server, data repository, and appropriate programming/instructions) and an Internet, PSTN, or other connection 108. As will be appreciated, in some embodiments, the raw data collected by controlling device 100 may be simply forwarded directly to monitoring service center 110 for evaluation and recording, while in other embodiments the data may be subjected to an initial evaluation locally within the controlling device itself or within STB 104 in order to ascertain the presence and if present, the severity of any out-of-range, health related data values. In such embodiments, the initial evaluation may then determine an action to be taken, ranging, for example, from repeating a test, through displaying a warning message on or by TV 102, to reporting an emergency situation to monitoring center 110. In such embodiments, all collected data may however still be reported to monitoring service center 110 on a lower priority or periodic basis regardless, for patient history recording purposes. Other variations of such a tiered response system are also possible, for example, evaluation of captured health related data values may be performed at an intermediate site such as cable system headend 106. In yet further embodiments, a controlling device equipped with for example WiFi or Bluetooth capability may report collected health related data directly to a monitoring service center 110 or to another local device such as a for example a PC for onward transmission to the monitoring service center 110.

Figure 2:
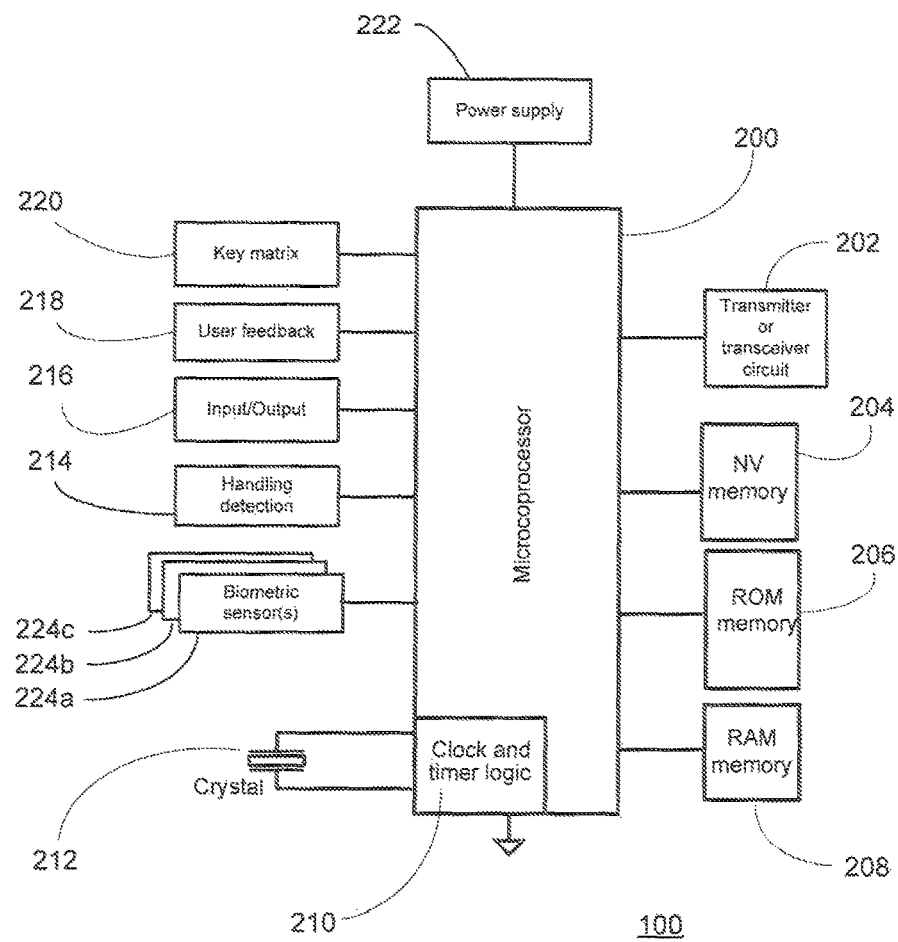
FIG. 2 illustrates a block diagram of exemplary components of the exemplary controlling device of FIG. 1.

With reference to FIG. 2, for use in commanding the functional operations of one or more appliances, the controlling device 100 may include, as needed for a particular application, a processor 200 coupled to a ROM memory 206, a RAM memory 208, a non-volatile read/write memory 204, a key matrix 220 (e.g., hard keys, soft keys such as a touch sensitive surface overlaid on a liquid crystal (LCD), and/or an electroluminescent (EL) display), transmission circuit(s) and/or transceiver circuit(s) 202 (e.g., IR and/or RF), a means 218 to provide feedback to the user (e.g., one or more LEDs, LCD, speaker, and/or the like), an input/output port 216 such as a serial interface, USB port, modem, Zigbee, WiFi, or Bluetooth transceiver, etc., a power source 222, and clock and timer logic 210 with associated crystal or resonator 212. Controlling device 100 may further include means 214 to detect that device 100 has been picked up and/or is being held by a user, for example a capacitance sensor, tilt switch, accelerometer, etc., and, in accordance with the subject system, various biometric sensors 224a, 224b, 224c capable of measuring, for example, one or more of pulse rate, skin temperature, skin moisture, blood glucose, hemoglobin oxygenation, etc., without limitation.

As will be understood by those skilled in the art, some or all of the memories 204, 206, 208 may include executable instructions (collectively, the controlling device program memory) that are intended to be executed by the processor 200 to control the operation of the device 100, as well as data which serves to define to the operational software the necessary control protocols and command values for use in transmitting command signals to controllable appliances (collectively, the command data). In this manner, the processor 200 may be programmed to control the various electronic components within the controlling device 100, e.g., to monitor the key matrix 220, to cause the transmission of signals, to enable power to and retrieve data from biometric sensors 224a/b/c, etc. The non-volatile read/write memory 204, for example an EEPROM, battery-backed up RAM, FLASH, Smart Card, memory stick, or the like, may additionally be provided to store setup information, data, and parameters as necessary. While the memory 206 is illustrated and described as a ROM memory, memory 206 can also be comprised of any type of readable media, such as ROM, FLASH, EEPROM, or the like. Preferably, the memories 204 and 208 are non-volatile or battery-backed such that data is not required to be reloaded after battery changes. In addition, the memories 204, 206 and 208 may take the form of a chip, a hard disk, a magnetic disk, an optical disk, and/or the like. Still further, it will be appreciated that some or all of the illustrated memory devices may be physically combined (for example, a single FLASH memory may be logically partitioned into different portions to support the functionality of memories 204 and 206 respectively), and/or may be physically incorporated within the same IC chip as the microprocessor 200 (a so called "microcontroller") and, as such, they are shown separately in FIG. 2 only for the sake of clarity.

To cause the controlling device 100 to perform an action, the controlling device 100 is adapted to be responsive to events, such as a sensed user interaction with the key matrix 220, etc. In response to an event, appropriate instructions within the program memory (hereafter the "controlling device operating program") may be executed. For example, when a function key is actuated on the controlling device 100, the controlling device 100 may retrieve from the command data stored in memory 204, 206, 208 a command value and control protocol corresponding to the actuated function key and, where necessary, the current device mode and transmit a command to an intended target appliance, e.g., TV 102, in a format recognizable by that appliance to thereby control one or more functional operations of that appliance. It will be appreciated that the operating program can be used not only to cause the transmission of commands and/or data to the appliances, but also to perform local operations. While not limiting, local operations that may be performed by the controlling device 100 may include displaying information/data, favorite channel setup, macro key setup, function key relocation, etc. Examples of local operations can be found in U.S. Pat. Nos. 5,481,256, 5,959,751, and 6,014,092. In addition, as described hereafter, local operations may include the activation, and monitoring of various biometric sensors, coupled with analysis and/or reporting of the data values obtained thereby.

In some embodiments, controlling device 100 may be universal, i.e., provided with a preprogrammed and/or downloaded library of appliance command data sets corresponding to appliances of different make, and/or model, and/or type thereby enabling a user to configure controlling device 100 to issue commands in a format recognizable by his particular appliances. Since such techniques and the methods by which a user may identify each intended target appliance to controlling device 100 are well known in the art, these will not be discussed further herein. Nevertheless, for additional information pertaining to setup procedures, the reader may turn, for example, to U.S. Pat. Nos. 4,959,810, 5,614,906, or 6,225,938 or to pending U.S. patent application Ser. No. 09/615,473 or 12/716,365 all of like assignee and all incorporated herein by reference in their entirety.

Figure 3:
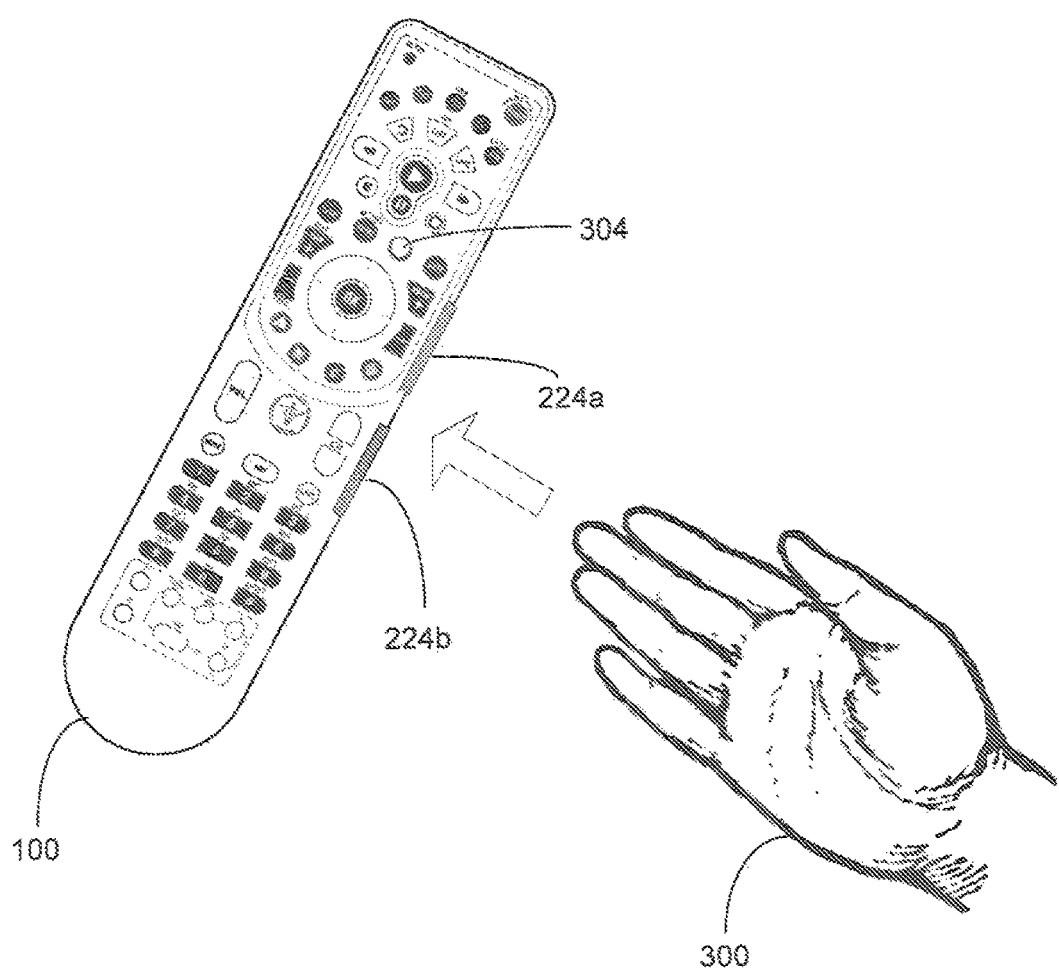
FIGS. 3 and 4 illustrate the exemplary controlling device of FIG. 1 in greater detail.
Figure 4:
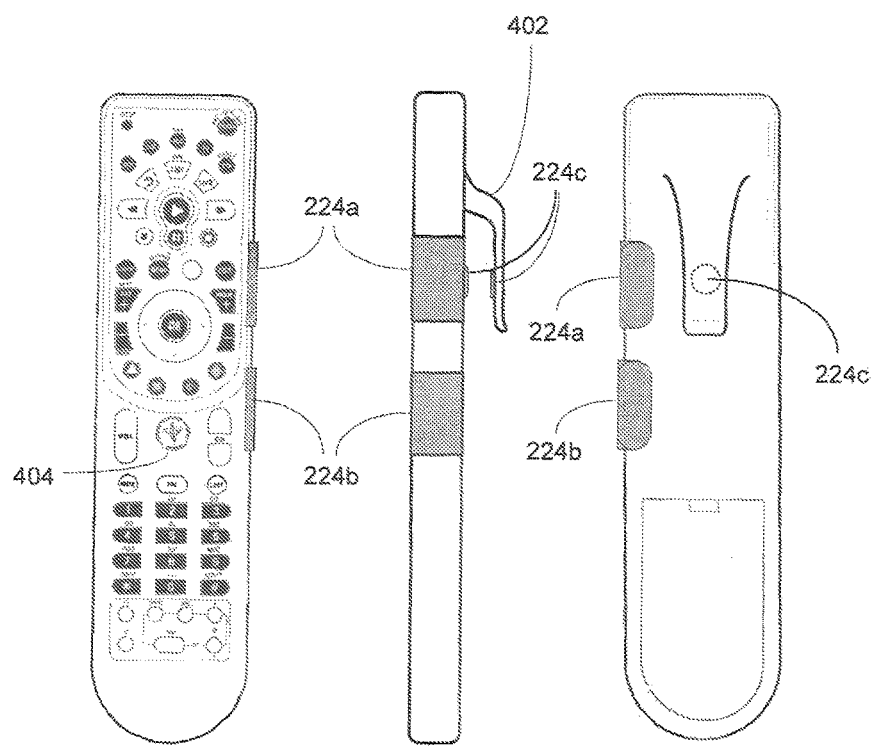

As illustrated in FIGS. 3 and 4, biometric sensors 224*a*, 224*b* and 224*c* may be positioned on the outer case or housing of controlling device 100, arranged such that they may come into contact with the hand 300 of a user when controlling device 100 is grasped in the usual manner of operation. It will be appreciated that although the placement of sensors 224*a* and 224*b* of the illustrative embodiment of FIGS. 3 and 4 is optimum for a right-handed user, in other embodiments left-handed users may be equally accommodated, for example by duplicating sensors on both sides of the controlling device, by locating a single set of sensors centrally on the underside of the controlling device 100, by providing separate left- and right-handed version of the controlling device 100, etc. Further, in those embodiments where the sensing technology to be used requires access to both sides of a hand or a hand part such as a finger, for example pulse oximetry or non-invasive blood glucose measurement techniques as described in U.S. Pat. No. 5,028,787 or 4,621,643, the housing of controlling device 100 may comprise an element arranged so as to encompass the desired body part when the controlling device is in the grasp of a user. By way of example, the underside of the illustrative controlling device 100 of FIG. 4 may comprise a cantilevered element 402 positioned such that during normal operation a user's finger(s) may be positioned between two constituent parts of biometric sensor 224*c*. It will be appreciated that such a cantilevered element may be fixed, flexible, hinged at the base and/or spring loaded, etc. as appropriate. In a like manner, in alternate embodiments the housing of a controlling device may a recess, opening, socket, or other suitable element into which a user's finger may be inserted to thereby position the user's finger between two constituent parts of a biometric sensor.

Figure 5:
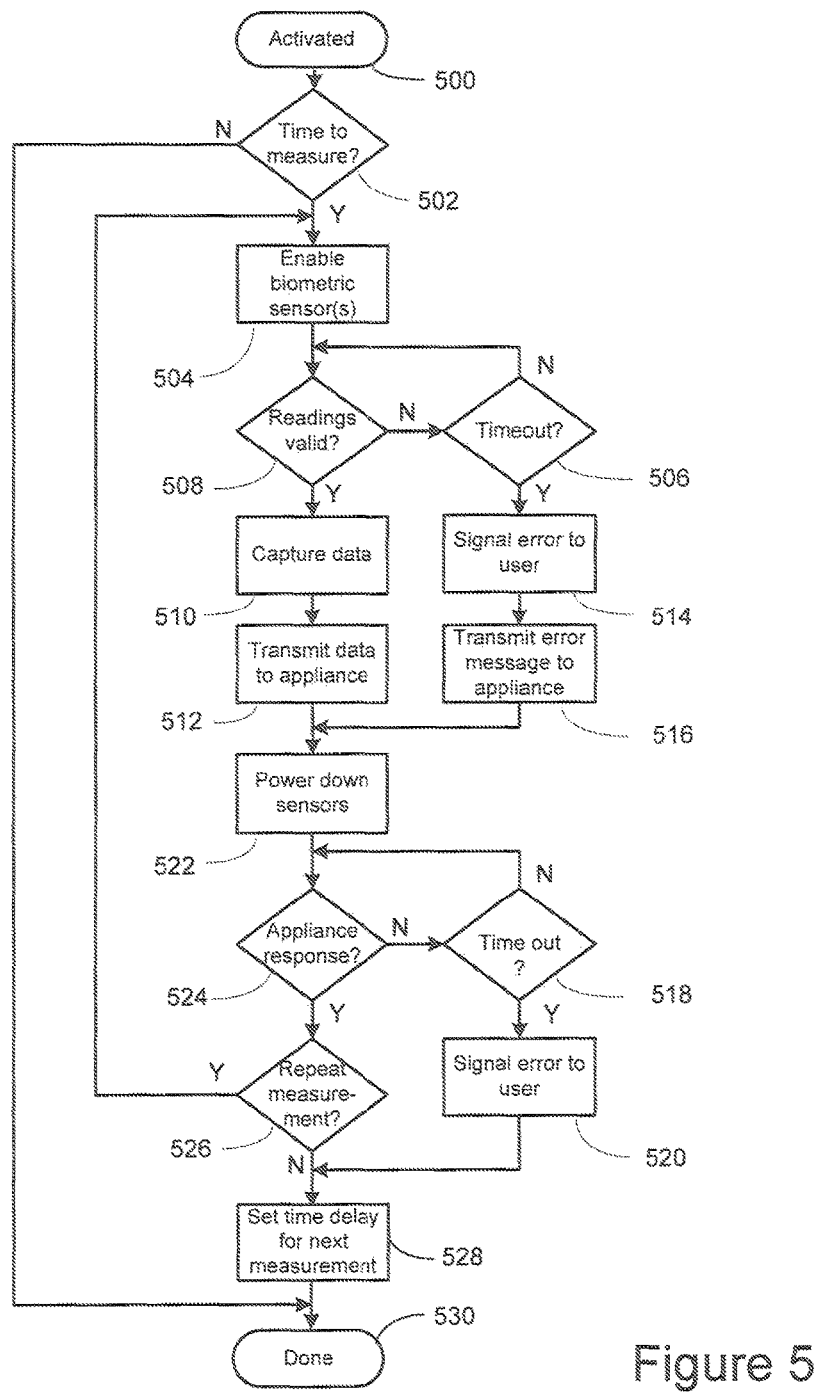
FIG. 5 illustrates in flowchart form an exemplary series of steps which may be performed by the operating software controlling device of FIGS. 1 and 2 to capture and report a user's biometric data.

An exemplary controlling device 100 may utilize biometric sensors such as 224*a*, 224*b*, 224*c* in support of a health monitoring service as will now be described in conjunction with the flowchart of FIG. 5. At step 500 a biometric data capture routine within the controlling device 100 operating program may be activated by one or more of a user picking up the controlling device, i.e., in response to an input from handling detection means 214; by user activation of an element of key matrix 220 either in the normal course of commanding the operation a controlled appliance or via a key 304 provided specifically for that purpose; by expiry of a timer; by receipt of a communication from a health monitoring application installed in or communicating through a target appliance, e.g., STB 104; etc., all as appropriate for a particular embodiment. Upon activation, at step 502 the controlling device operating program may first ascertain the elapsed time since the previous measurement cycle. If this time is less than a specified minimum interval (which interval may be predetermined, user adjustable, communicated from a target appliance such as STB 104, etc.) then no measurement is currently due and the controlling device operating program may exit the biometric data capture routine at step 530. In this manner, the battery life of controlling device 100 may be conserved and the reporting path 104, 106, 108 not overloaded with data. In some embodiments the test of step 502 may however be omitted, for example, where the activation is in response to a request communicated from a target appliance on behalf of a health monitoring application which is itself responsible for determining the measurement interval or in response to a user input provided to the controlling device 100 that indicates an affirmative desire to capture such data.

If it is determined that a biometric measurement cycle is due, at step 504 the controlling device 100 operating program may enable exemplary biometric sensors 224*a*, 224*b*, and 224*c* and then at steps 508/506 may wait a suitable period of time for the sensors to stabilize and produce valid readings. Once valid data is detected from biometric sensors 224*a*, 224*b* and/or 224*c*, at steps 510 and 512 this data is captured and transmitted to a consumer appliance that is specified to receive the biometric monitoring data, e.g., STB 104. In the case of a universal controlling device 100, such captured data would be transmitted to the consumer appliance via selection and use of an appropriate protocol by the controlling device 100. If no valid readings are detected within the allotted time interval, the data capture cycle may be abandoned and at steps 514, 516 an error may be signaled to the user, e.g., via user feedback means 218, and an error message transmitted to the receiving appliance. Upon either completion or abandonment of the data capture cycle, at steps 522 and 524/518 the controlling device 100 operating program may disable exemplary biometric sensors 224*a*, 224*b*, and 224*c* and thereafter wait for a response from the receiving appliance. If no response is received within the allotted time interval, at step 520 an error is signaled to the user, e.g., via user feedback means 218 and processing continues at step 528 as will be further described hereafter. When a response is obtained from the receiving appliance, at step 526 the controlling device operating program may determine if the response comprises a request for a repeat measurement. By way of explanation, in the exemplary system illustrated in FIG. 1, such a request may be issued for example by a receiving appliance such as STB 104 in response to a "invalid reading" error message (step 516) from controlling device 100, in conjunction with display by STB 104 of a message on the screen of TV 102 requesting that the user reposition his grasp of controlling device 100. In other instances such a request for an immediate repeat reading may be issued by a monitoring algorithm resident in STB 104, cable system headend 106, or monitoring service center 110 following receipt of biometric data indicative of a possibly critical condition of the user of controlling device 100. If such a repeat request is received, the controlling device 100 operating program may resume the biometric measurement sequence at step 504 as illustrated. If no repeat is requested, at step 528 the controlling device 100 operating program may reset the minimum interval time to be used in a future step 502, after which processing is complete. It will be appreciated that the minimum interval time used in step 528 may comprise a predetermined fixed value, may be user adjustable, may be determined by the receiving appliance and embedded in the response of step 524, etc.

Figure 6:
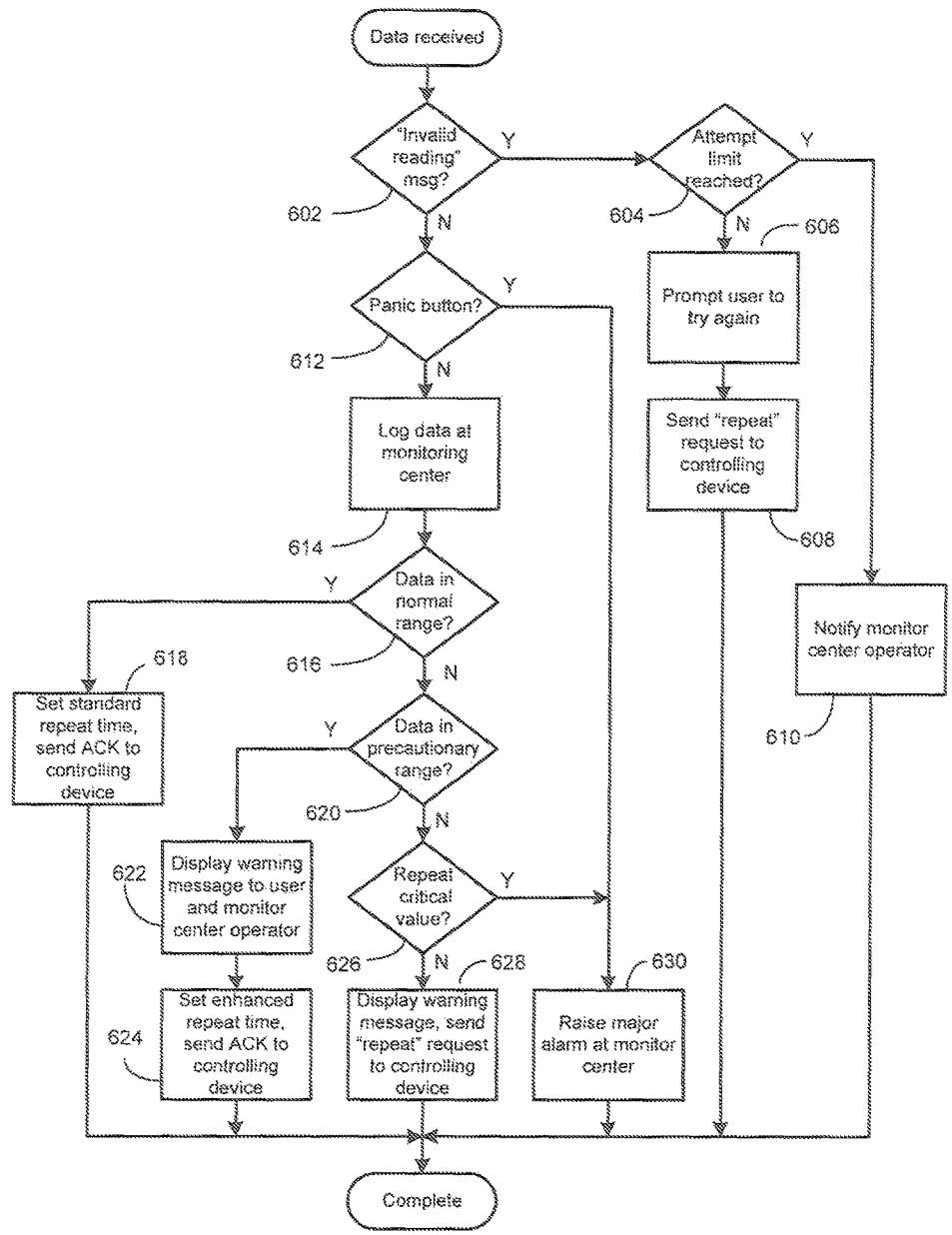
FIG. 6 illustrates in flowchart form an exemplary method for monitoring a user's health status based upon biometric data provided by the controlling device of FIGS. 1 and 2.

FIG. 6 presents an exemplary method for implementing a health monitoring system and service utilizing the output of a biometric sensor equipped controlling device 100. In reviewing this figure it should be appreciated that the individual steps of the method may be performed at any of various physical locations or tiers of the system as convenient for a particular implementation. For example, in the case of the illustrative system of FIG. 1 some or all of the steps of the method may be performed at any of cable STB 104, cable headend 106, central monitoring site 110, etc., as appropriate for the specific implementation selected by the provider of the service. Accordingly, in the description that follows any mention of a particular location for performance of a step is intended to be exemplary and not limiting.

Upon receipt of a transmission from a biometric sensor equipped device such as exemplary controlling device 100, at step 602 the method may initially determine if the transmitted message comprises an "invalid reading" status. If so, at step 604 it may next be determined if this report has reached a limit established for repeated attempts to correct ongoing measurement failures. If not, at step 606 a corrective message may be conveyed to a user of the controlling device 100, for example a prompt displayed on or by TV 102 requesting that a user adjust their grasp of controlling device 100, followed at step 608 by a request to the controlling device 100 to repeat the measurement attempt. If, however, the limit for such actions has been reached without success, then at step 610 an alert and notification of measurement failure may issued to an operator located at a centralized monitoring service center, e.g. 110 of FIG. 1.

If a received message from a biometric sensor equipped device is determined to comprise valid data, at step 612 it is next determined if the message comprises a signal that an emergency alert ("panic button"), e.g. key 404 of exemplary controlling device 100, has been activated by a user. If so, at step 630 an alarm may immediately be raised at monitoring service center 110. If not, at step 614 the received data may next be logged at monitoring service center 110 for patient history recording purposes. Next, at step 616 it is determined if the received biometric data values fall within a normal range. As will be appreciated the system and methods described herein may readily be adapted to support health monitoring services for multiple individuals at the same location, for example by the provision of multiple addressable sensor-equipped controlling devices, by use of one or more of the biometric measurements as a means to distinguish between users, etc. Accordingly, in certain embodiments this normal range of values may be individually established for each particular user of a biometric sensor equipped device. In such embodiments multiple users of a single device or single reporting channel may be identified via the use of biometric measurements, individualized devices, explicit user input to identify each individual user, etc. In this regard see for example U.S. Pat. Nos. 6,906,696, 7,236,156 or 7,266,701 all of which are incorporated herein by reference in their entirety.

If the received biometric data is within normal range(s), then at step 618 the measurement repetition interval is set to its standard value (which interval may be determined on an individual user basis and/or may be dependent on the specific type(s) of biometric values being monitored) and an acknowledgement response issued to the controlling device 100. It will be appreciated that in the case of a controlling device 100 which directly measures repetition intervals, as contemplated for example by step 528 of FIG. 5, the acknowledgement response may incorporate a parameter to indicate this interval. Alternatively, the desired interval may be timed elsewhere, e.g. at STB 104, cable head end 106 or monitoring service center 110 and explicit request(s) issued to the monitoring controlling device 100 as appropriate.

If it is determined that the received biometric data values fall outside a normal range, then at step 620 of the exemplary method, it is next determined if the data values fall within a precautionary range. Such precautionary range(s) may be established for various biometric parameters and may trigger enhanced monitoring services, for example conveying a warning message to the user and/or a monitoring center operator together with an increased frequency of measurement, as illustrated at steps 622 and 624. Once again, such ranges may be individually established for each user of the service.

If however, one or more of the received biometric data values falls outside the established precautionary range a critical condition may exist. In the exemplary method illustrated, in order to prevent false alarms such an out of range value may trigger an immediate request to the biometric measuring device to repeat the measurement as illustrated at step 628. If the second measurement remains out of range, a major alarm may be raised at the monitoring service center as illustrated at steps 626 and 630. It will however be appreciated that in other embodiments a critically out of range measurement may trigger an immediate alarm at a monitoring center, leaving the decision to repeat the measurement in the hands of the monitoring service operator.

Figure 7:
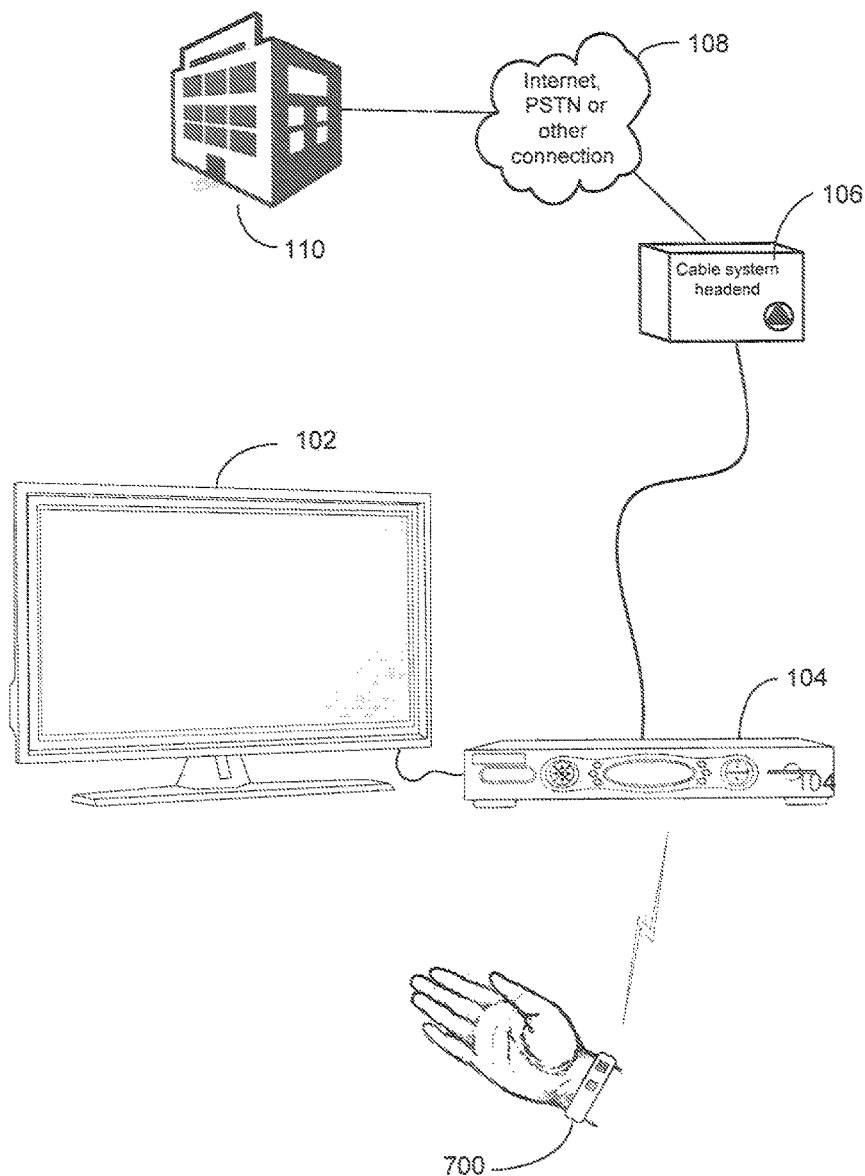
FIG. 7 illustrates an alternative system embodiment in which health status monitoring and reporting via a consumer appliance such as a STB may be implemented.

While various concepts have been described in detail, it will be appreciated by those skilled in the art that various modifications and alternatives to those concepts could be developed in light of the overall teachings of the disclosure. For example, while one embodiment presented herein is described in terms of an exemplary hand-held controlling device intended for use in conjunction with a consumer appliance such as TV or STB, it will be appreciated that a similar functionality may be offered in other portable devices, for example a remote control intended for use with a home security system, without departing from the spirit of this invention. In an exemplary alternative embodiment which is illustrated in FIG. 7, a wearable device such as a bracelet 700 may comprise biometric sensors and associated circuitry and programming similar to that described above in connection with the biometric monitor portions of exemplary controlling device 100. Bracelet 700 may be offered in conjunction with a health monitoring service such as described above in connection with FIG. 6, either in place of or as a supplement to a biometric sensor enabled controlling device. Alternatively, in some embodiments biometric sensors may comprise part of a wrist strap or safety retaining tether provided in conjunction with a controlling device, such as for example a Nintendo brand Wii controller.

Further, while described in the context of functional modules and illustrated using block diagram format, it is to be understood that, unless otherwise stated to the contrary, one or more of the described functions and/or features may be integrated in a single physical device and/or a software module, or one or more functions and/or features may be implemented in separate physical devices or software modules. It will also be appreciated that a detailed discussion of the actual implementation of each module is not necessary for an enabling understanding of the invention. Rather, the actual implementation of such modules would be well within the routine skill of an engineer, given the disclosure herein of the attributes, functionality, and inter-relationship of the various functional modules in the system. Therefore, a person skilled in the art, applying ordinary skill, will be able to practice the invention set forth in the claims without undue experimentation. It will be additionally appreciated that the particular concepts disclosed are meant to be illustrative only and not limiting as to the scope of the invention which is to be given the full breadth of the appended claims and any equivalents thereof.

All patents cited within this document are hereby incorporated by reference in their entirety.

What is claimed is:

1. A hand-held controlling device for use in controlling functional operations of one or more controllable consumer appliances, comprising:
   a processing device;
   a wireless transmitter coupled to the processing device;
   a user interface having a plurality of input elements coupled to the processing device; and
   at least one biometric sensor coupled to the processing device;
   wherein, in response to the processing device determining that one or more of the plurality of input elements of the user interface has been activated to cause the wireless transmitter to transmit commands to control a functional operation of one or more of the controllable consumer appliances while the at least one biometric sensor is in a disabled state, the processing device functions to transition the at least one biometric sensor from the disabled state to an enabled state to thereby allow for biometric data to be captured from a user via use of the least one biometric sensor.

2. The hand-held controlling device as recited in claim 1, further comprising an output device coupled to the processing device wherein the processing device receives signals from the at least one biometric sensor and causes the output device to present information to the user related to biometric data captured from the user.

3. The hand-held controlling device as recited in claim 1, wherein the controlling device comprises a housing having a first housing element and a second housing element between which a finger of the user is to be inserted as the user holds the hand-held controlling device and wherein constituent parts of the at least one biometric sensor are located on each of the first housing element and the second housing element.

4. The hand-held controlling device as recited in claim 3, wherein one of the first housing element and the second housing element comprises a cantilevered element associated with the housing.

5. The hand-held controlling device as recited in claim 4, wherein the cantilevered element is located on a bottom side of the housing and wherein a top side of the housing opposite the bottom side of the housing carries the user interface.

6. The hand-held controlling device as recited in claim 1, wherein the processing device receives signals from the at least one biometric sensor and causes the wireless transmitter to transmit a communication having data related to biometric data captured from the user.

7. The hand-held controlling device as recited in claim 1, further comprising a wireless receiver coupled to the processing device wherein the wireless receiver is used to receive a request from at least one of the controllable consumer appliances to have the at least one biometric sensor capture biometric data from the user.

8. The hand-held controlling device as recited in claim 1, further comprising a timing device coupled to the processing device wherein an expiration of predetermined time interval as measured by the timing device is used as a request to have the at least one biometric sensor capture biometric data from the user.

9. The hand-held controlling device as recited in claim 1, wherein the user interface further comprises a panic button activatable to cause the processing device to issue an emergency alert communication via the wireless transmitter.

10. The hand-held controlling device as recited in claim 9, further comprising an output device coupled to the processing device wherein the processing device receives signals from the at least one biometric sensor and causes the output device to present information to the user related to biometric data captured from the user.

11. The hand-held controlling device as recited in claim 9, wherein the controlling device comprises a housing having a first housing element and a second housing element between which a finger of the user is to be inserted as the user holds the hand-held controlling device and wherein constituent parts of the at least one biometric sensor are located on each of the first housing element and the second housing element.

12. The hand-held controlling device as recited in claim 11, wherein one of the first housing element and the second housing element comprises a cantilevered element associated with the housing.

13. The hand-held controlling device as recited in claim 12, wherein the cantilevered element is located on a bottom side of the housing and wherein a top side of the housing opposite the bottom side of the housing carries the user interface.

14. The hand-held controlling device as recited in claim 9, wherein the processing device receives signals from the at least one biometric sensor and causes the wireless transmitter to transmit a communication having data related to biometric data captured from the user.

15. The hand-held controlling device as recited in claim 9, further comprising a wireless receiver coupled to the processing device wherein the wireless receiver is used to receive a request from at least one of the controllable consumer appliances to have the at least one biometric sensor capture biometric data from the user.

16. The hand-held controlling device as recited in claim 9, further comprising a timing device coupled to the processing device wherein an expiration of predetermined time interval as measured by the timing device is used as a request to have the at least one biometric sensor capture biometric data from the user.

17. A hand-held controlling device for use in controlling functional operations of one or more controllable consumer appliances, comprising:
 a processing device;
 a wireless transmitter coupled to the processing device;
 a handling sensor coupled to the processing device for generating a signal in response to a detected handling of the hand-held controlling device by a user;
 a user interface having a plurality of input elements coupled to the processing device wherein one or more of the plurality of input elements are activable to cause the processing device to instruct the wireless transmitter to transmit commands to control a functional operation of one or more of the controllable consumer appliances; and
 at least one biometric sensor coupled to the processing device;
 wherein, in response to the processing device receiving from the handling sensor the signal generated in response to the detected handling of the hand-held controlling device by the user while the at least one biometric sensor is in a disabled state, the processing device functions to transition the at least one biometric sensor from the disabled state to an enabled state to thereby allow biometric data to be captured from the user via use of the least one biometric sensor.

18. The hand-held controlling device as recited in claim 17, wherein the handling sensor comprises an accelerometer.

19. The hand-held controlling device as recited in claim 17, wherein the user interface further comprises a panic button activatable to cause the processing device to issue an emergency alert communication via the wireless transmitter.

* * * * *